United States Patent
Hegenbarth et al.

(10) Patent No.: US 11,428,923 B2
(45) Date of Patent: Aug. 30, 2022

(54) NEGATIVE LENS AND ENDOSCOPE OBJECTIVE

(71) Applicant: Karl Storz SE & Co. KG, Tuttlingen (DE)

(72) Inventors: Robin Hegenbarth, Tuttlingen (DE); Walter Vogel, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 317 days.

(21) Appl. No.: 16/863,213

(22) Filed: Apr. 30, 2020

(65) Prior Publication Data

US 2020/0264424 A1 Aug. 20, 2020

Related U.S. Application Data

(63) Continuation of application No. 15/818,942, filed on Nov. 21, 2017, now Pat. No. 10,725,282.

(30) Foreign Application Priority Data

Nov. 22, 2016 (DE) .......................... 102016122429.4
Nov. 15, 2017 (EP) ..................................... 17001867

(51) Int. Cl.
*G02B 23/24* (2006.01)
*G02B 3/00* (2006.01)
*A61B 1/00* (2006.01)
*G02B 23/02* (2006.01)

(52) U.S. Cl.
CPC ........ *G02B 23/243* (2013.01); *A61B 1/00096* (2013.01); *A61B 1/00179* (2013.01);
(Continued)

(58) Field of Classification Search
CPC ........ G02B 23/243; G02B 3/00; G02B 23/02; G02B 2003/0093; A61B 1/00096; A61B 1/00179
See application file for complete search history.

(56) References Cited

U.S. PATENT DOCUMENTS 4,815,833 A 3/1989 Zobel et al.
4,850,342 A 7/1989 Hashiguchi et al.
(Continued)

FOREIGN PATENT DOCUMENTS

DE 19736617 A1 3/1999
DE 102004042023 A1 3/2006
(Continued)

OTHER PUBLICATIONS

German Search Report Application No. DE 10 2016 122 429.4 dated Sep. 18, 2017 8 pages.
(Continued)

*Primary Examiner* — James C. Jones
(74) *Attorney, Agent, or Firm* — Michael J. Loi; David Noel Villalpando

(57) ABSTRACT

A negative lens, for an oblique-view endoscope objective, has a first face with a first optical surface and a second face with a second optical surface opposing the first optical surface, the second optical surface being a concave optical surface, wherein a recess is formed in the second face adjacent to the concave optical surface. An endoscope objective, that includes a deflection prism having an entrance face and further including a negative lens, the negative lens having a first face with a first optical surface and a second face with a second optical surface opposing the first optical surface, the second optical surface being a concave optical surface. The negative lens is mounted on a distal planar surface of the deflection prism such that a rim encompassing the concave optical surface abuts the distal planar surface of the deflection prism.

20 Claims, 5 Drawing Sheets

(52) U.S. Cl.
CPC ............... *G02B 3/00* (2013.01); *G02B 23/02* (2013.01); *G02B 2003/0093* (2013.01)

(56) References Cited

U.S. PATENT DOCUMENTS

| | | | |
|---|---|---|---|
| 5,051,824 A | 9/1991 | Nishigaki | |
| 5,980,453 A | 11/1999 | Forkey et al. | |
| 6,635,010 B1 | 10/2003 | Lederer | |
| 2011/0242807 A1 | 10/2011 | Little, Jr. et al. | |
| 2012/0140336 A1* | 6/2012 | Fujino | G02B 19/0033 359/654 |

FOREIGN PATENT DOCUMENTS

| | | |
|---|---|---|
| EP | 2165640 A1 | 3/2010 |
| JP | S56128914 A | 10/1981 |

OTHER PUBLICATIONS

Partial European Search Report Application No. EP17001867 Completed: Apr. 18, 2018 10 pages.

European Search Report Application No. EP17001867 Completed: Jun. 25, 2018; dated Jul. 9, 2018 12 pages.

L Reference Delivery Note 37 Pages.

European Notice of Opposition and Translation Application No. 17001867.5 Completed: Feb. 7, 2020 29 Pages.

U.S. Office Action U.S. Appl. No. 15/818,942 dated Sep. 20, 2019 10 Pages.

V Reference 89544520, Optical Design of HSW Laryngoscope 8 Pages.

Henke Sass Wolf, "Med-line endoscopes," promotional literature, pp. 1-5, Sep. 2010, Henke-Sass Wolf GmbH, Tutlingen, Germany.

* cited by examiner

NEGATIVE LENS AND ENDOSCOPE OBJECTIVE

TECHNICAL FIELD

The present invention relates to a negative lens having a first face with a first optical surface and a second face with a second optical surface opposing the first optical surface, the second optical surface being a concave optical surface. Further, the invention relates to an endoscope objective comprising a deflection prism, the deflection prism having an entrance face, and a negative lens, the negative lens having a first face with a first optical surface and a second face with a second optical surface opposing the first optical surface, the second optical surface being a concave optical surface.

BACKGROUND

Endoscopic examination techniques have prevailed in a multiplicity of medical and veterinary fields of application, as well as in many non-medical fields. In such examination techniques, an endoscope, which has an elongate shaft with an imaging optical system, is introduced into an internal cavity of a human or animal body or another object to be examined. The elongate shaft that is configured for being inserted into the cavity of the body or other object may be rigid, semi-rigid or flexible. In a distal (i.e. distant from a user) end section of the elongate shaft an endoscope objective is arranged for generating in an image plane an image of an object field in the cavity of the body or object, wherein the endoscope objective typically comprises one or more negative lenses. The generated image is transmitted to a proximal (i.e. close to a user) end of the endoscope for being viewed by the user or picked up by an electronic image sensor which is connected to a display and/or storage device. For transmitting the image from the distal to the proximal end section of the endoscope, the elongate shaft may comprise a fiber optic image guide or a sequence of relay lenses. Alternatively, the image generated by the endoscope objective may be picked up by an electronic image sensor arranged in the distal end section of the shaft and transmitted electronically towards the proximal end section of the endoscope.

Depending on an intended application, endoscopes with various viewing angles are known. In particular, oblique-view endoscopes are known which have a viewing direction that deviates from a longitudinal axis of the shaft. Such oblique-view endoscopes typically have a rigid shaft the distal end of which comprises a cover glass mounted at an oblique angle in a distal opening of the shaft. The cover glass forms a distal window for light rays coming from the object field and entering into the endoscope objective. The objective of such an oblique-view endoscope usually comprises one or several lenses and at least one deflection prism for deflecting light entering at an oblique angle through the distal window into the objective in a direction parallel or almost parallel to the longitudinal axis of the shaft. According to a well-known optical design of objectives for oblique-view endoscopes, the incident light rays, after passing through the cover glass and a first group of objective lenses, enter into the deflection prism through an obliquely arranged entrance face of the deflection prism. On their path through the deflection prism, the rays are reflected twice. The first reflection occurs on a first reflective plane of the deflection prism which is oblique to the longitudinal axis, the rays being reflected back towards the entrance face. The second reflection, which may be a total internal reflection, occurs on the entrance face, which serves as a second reflective plane. After the second reflection, the incident light rays have a direction for entering into another group of objective lenses, being focused in an image plane of the endoscope objective for forming an image of the object field.

According to this optical design, the entrance face of the deflection prism has a twofold function. First, it must permit transmission of the incident rays so that the rays can pass towards the first reflective plane, and second, it must permit reflection, preferably total reflection, of the rays being reflected back by the first reflective plane into a desired direction, which is generally parallel to the longitudinal axis. In order to permit total reflection and to guarantee low losses, the entrance face must provide a sufficient difference of refractive indices from the inside to the outside the deflection prism.

In U.S. Pat. No. 4,815,833, an objective for endoscopes is disclosed comprising an elongated prism on a distal end of which are joined by cementing a diaphragm and a negative lens. A wedge-shaped angular diaphragm, made from metal or opaque glass, is cemented directly to an obliquely cut surface of the distal end portion of the prism. The negative lens is cemented to the distal side of the diaphragm. The image beam from the lens passes through a central opening of the diaphragm and through a surface of the prism that does not have a reflective coating. The beam then strikes another surface of the prism and is reflected back to the first mentioned surface. This time, the angle of incidence is so large that total internal reflection takes place and the image beam is projected along the axis of the prism.

In U.S. Pat. No. 4,850,342, a hard endoscope of oblique-view type is described in which an objective front lens is arranged in parallel with a plane of a cover glass at a slight gap and is fixed to an objective prism with a frame.

Further, it is known to arrange a keyhole-shaped diaphragm between the deflection prism and a negative lens mounted on the deflection prism, in order to provide an air layer on the first surface of the deflection prism that is employed for total reflection.

The positioning of a diaphragm or a frame between the deflection prism and the negative lens is problematic and may increase production cost. Further, dust grains may be caught, reducing the optical quality of the objective.

According to DE 197 36 617 A1, in an endoscope objective having a direction of view including an angle different from zero with the longitudinal axis of the endoscope, on a surface of a prism unit a thin layer is deposited having a refractive index that is smaller than the refractive index of the material of the prism unit. The thin layer provides for total reflection on the corresponding surface of the prism unit. Thus, if an optical element of the objective is placed on the thin layer, no mechanical spacer is needed. However, the thin layer may lead to an increase of production cost, may have non-optimal anti-reflection properties, and the refractive index of the thin layer may undesirably limit the range of incidence angles at which total reflection occurs.

It is therefore an object of the present invention to provide a negative lens and an endoscope objective which alleviate the above mentioned problems. In particular, it is an object of the invention to provide a negative lens for an endoscope objective that can be mounted on a surface of a deflection prism of the endoscope objective in a cost-saving and efficient manner without deteriorating the image quality. It is another object of the present invention to provide an endoscope objective comprising a negative lens that can be assembled in a cost-saving and efficient manner without deterioration of the image quality.

These objects are met by a negative lens and an endoscope objective according to the invention.

SUMMARY

According to a first aspect of the present invention, a negative lens is provided, i.e. a lens having negative refractive power. Preferably, the negative lens is a single lens. However, the negative lens may be a cemented doublet or triplet having overall negative refractive power. The negative lens has a first face having a first optical surface, and a second face having a second optical surface, the first and second optical surfaces being arranged in an opposed relationship, such that light impinging on the first optical surface at a limited angle to an optical axis of the lens passes through the lens and exits the lens through the second optical surface. The optical axis is an axis of symmetry of the optical surfaces. The negative lens is made of a transparent material, in particular optical glass. The second optical surface is a concave optical surface, preferably having spherical shape. The first and/or second optical surfaces of the negative lens may have an anti-reflective coating.

In accordance with the present invention, a recess is formed in the second face, the recess being adjacent to the concave optical surface. In particular, a surface of the recess is joined to the concave optical surface or forms a continuation of the concave optical surface. The concave optical surface and the surface of the recess may merge to form a continuous surface.

When the negative lens is mounted on a planar surface with its second face being directed towards the planar surface, the concave optical surface forms a cavity, and the recess forms a continuation of the cavity or, in other words, the cavities formed by the concave optical surface and by the recess merge to form an enlarged combined cavity. The combined cavity may be filled with air, thus forming an air layer on the planar surface. When the planar surface upon which the negative lens is mounted is a surface of an optical element employed for internal total reflection, the air layer serves to provide a small refractive index outside the optical element and thus a large difference of refractive indices between the inside and the outside of the optical element. This permits a large range of incidence angles of rays being totally internally reflected on the planar surface of the optical element. Further, as the recess serves to enlarge the cavity defined by the concave optical surface and thus serves to enlarge the area of the planar surface covered by the air layer, the total area of the planar surface of the optical element available for total internal reflection is enlarged. This permits an enlarged fraction of rays transmitted inside the optical element to the planar surface to be totally internally reflected. The negative lens may be configured for being directly mounted on the planar surface of the optical element, a partial area of the second face touching the planar surface.

Preferably, the negative lens is configured for being employed in an objective of an endoscope, in particular in the objective of an oblique-view endoscope. The negative lens may be configured for being arranged on an entrance face of a deflection prism of the endoscope objective, in particular for being cemented directly onto the entrance face, such that the entrance face is crossed by the incident rays and, after a first reflection, the rays are totally internally reflected on the same surface of the deflection prism. When the negative lens is mounted on the entrance of the deflection prism, the ability of the objective to collect incident light and to form an image of an object field is improved. Due to the increased fraction of the surface of the prism that can be employed for total reflection, the negative lens according to the invention permits a more convenient design of the optical system. Further, the negative lens can be mounted in a simple and efficient manner on the deflection prism forming a stable unit.

Preferably, the negative lens is a plano-concave lens. A plano-concave lens is particularly suitable for being used in an oblique-view endoscope objective and, in particular, for being cemented on the entrance face of the deflection prism of an oblique-view endoscope objective. In a plano-concave lens, the optical axis is perpendicular to the first optical surface, which is a planar surface, and crosses the concave optical surface in its apex. Alternatively, the negative lens may be a bi-concave lens or a negative meniscus lens.

Advantageously, the negative lens on its second face exhibits a rim encompassing the concave optical surface and the recess, the rim having a planar surface. The second face of the negative lens thus is formed by the concave optical surface, the surface of the recess being interconnected to the concave optical surface, and the planar surface of the rim. If the recess is formed by removing lens material out of the second face of the negative lens, the rim may be considered a remaining part of the second face that protrudes over the concave optical surface and the surface of the recess. Preferably, the rim forms a closed ring, and the planar surface is a closed surface encompassing the concave optical surface and the recess. In particular, the planar surface of the rim is perpendicular to the optical axis of the lens. The planar surface of the rim is particularly suitable for cementing the negative lens upon a planar surface, for example on the entrance face of a deflection prism of an oblique-view endoscope objective, being flush with the surface of the deflection prism. In this way, most secure fixation of the negative lens on the planar surface is facilitated.

According to a preferred embodiment of the invention, the recess is configured asymmetrically with respect to the concave optical surface, and, in particular, asymmetrically with respect to the optical axis of the negative lens. Advantageously, the recess extends from the concave optical surface in one lateral direction only or predominantly, thereby enlarging in the lateral direction the cavity formed by the concave optical surface when the negative lens is mounted on a planar surface. The recess thus serves to enlarge the area of a planar surface of an optical element usable for total internal reflection, if the negative lens is arranged on the surface with the recess extending in such a lateral direction in which rays to be totally internally reflected are displaced with respect to the optical axis of the negative lens.

According to an alternative embodiment of the invention, the recess is configured symmetrically with respect to the concave optical surface, i.e. symmetrically with respect to the optical axis of the negative lens. In this case, the rim can be considered forming a ring-shaped base of the negative lens on its second face. When a negative lens having a symmetric recess is mounted on a planar surface of an optical element, the fraction of the surface that can be used for total reflection is enlarged.

Preferably, the recess is a step-shaped depression. If the recess is asymmetric, the step may merge into the concave optical surface. If the recess is symmetric, the step may be circular, encompassing the concave optical surface in a symmetric manner. A step-shaped depression in the second face of the negative lens can be manufactured easily and provides a well-defined extension of the cavity formed by the concave surface.

Advantageously, a back-surface of the recess is a planar surface. In this way a well-defined air layer is provided if the negative lens is mounted on a planar surface. The back-surface preferably is polished for avoiding dust and to facilitate clean assembly, but need not necessarily be of optical quality.

Preferably, the negative lens is formed in one piece. In particular, the negative lens may be manufactured by grinding out of one block of transparent material. In this way, manufacturing is facilitated and stability is enhanced.

In accordance with a further aspect of the present invention an endoscope objective is provided that comprises a deflection prism and a negative lens, in particular an oblique-view endoscope objective is provided. The negative lens preferably is a single lens, but may be a cemented doublet or triplet having overall negative refractive power. The negative lens has a first face with a first optical surface and a second face with a second optical surface opposing the first optical surface. The second optical surface is a concave optical surface, preferably a spherical surface. The deflection prism has an entrance face and an exit face. The entrance face and/or the exit face may exhibit an anti-reflective coating. The negative lens is arranged to a distal side of the entrance face of the deflection prism. The deflection prism has at least two reflective planes, one of which is formed by the entrance face. A first reflective plane may be arranged for at least partially reflecting light rays having entered through the entrance face into the deflection prism, in a partially backwards direction towards the entrance face. The entrance face, which forms the second reflective plane, preferably is arranged for reflecting by total internal reflection light rays coming from the first reflective plane towards the exit face. The exit face of the deflection prism may be a planar surface perpendicular to a longitudinal axis of the endoscope objective. The endoscope objective further comprises a proximal lens group arranged on a proximal side of the deflection prism, the proximal lens group having overall positive refractive power for generating an image of the object field in an image plane. The endoscope objective may comprise a cover glass arranged on a distal side of the negative lens. The endoscope objective may comprise further elements, such as spacers and diaphragms.

In accordance with this aspect of the invention, the negative lens is mounted on the entrance face of the deflection prism such that a rim encompassing the concave optical surface of the second face of the lens abuts the entrance face of the deflection prism. In particular, the negative lens is directly mounted on that planar surface that forms the entrance face of the deflection prism. Preferably the negative lens is directly cemented onto the planar surface, i.e. the rim directly touches the planar surface of the deflection prism or is separated only by a layer of optical cement from the planar surface, wherein the latter may have an anti-reflective coating. Therefore the concave optical surface of the second face of the negative lens and the entrance face of the deflection prism form a cavity that typically is filled with air, thus forming an air layer on the planar surface.

The negative lens serves to collect rays coming from an object field to be observed, allowing for a large field of view. After having passed the negative lens, the rays enter into the deflection prism through the entrance face of the deflection prism. Thereafter rays are reflected internally in a partially backward direction towards the entrance face. In particular the rays are reflected by the first reflective plane towards the entrance face. On the entrance face, i.e. on the second reflective plane, total internal reflection occurs. By total internal reflection the rays preferably are directed towards the exit face of the deflection prism. Having exited the deflection prism through the exit face, the rays may enter into the proximal lens group, being focused in the image plane. The endoscope objective is designed such that the rays coming from the object field and having been internally reflected in the deflection prism towards the entrance face impinge on the entrance face in an area of the entrance face covered by the air layer formed by the concave optical surface of the second face of the negative lens.

Due to the rays being internally reflected on the entrance face of the deflection prism in that part of its surface on the distal side of which the air-filled cavity is situated, a high difference between refractive indices inside and outside the deflection prism is provided, thus enhancing total reflection. Further, appropriate positioning of the air-filled cavity is facilitated by mounting the negative lens on the entrance face of the deflection prism, for example by directly cementing the negative lens upon the entrance face. In this way, an endoscope objective is provided that has improved characteristics regarding the ability to collect incident rays from the object field and to form an image of the object field, and that can be assembled in a simple, stable and cost-efficient manner.

Preferably, the negative lens is a negative lens as described above. In this case the combined cavity and the entrance face of the deflection prism form a cavity resulting in an air layer on the entrance face of the deflection prism, the combined cavity being formed by the concave optical surface of the second face of the negative lens and by the recess. In this way, the area of the entrance face usable for total internal reflection is increased.

In particular, the endoscope objective is an oblique-view endoscope objective, i.e. is configured as an objective for an oblique-view endoscope, which may be a medical or a non-medical endoscope. The entrance face of the deflection prism may be arranged at an angle to a longitudinal axis of the endoscope objective. The oblique-view endoscope may be a rigid endoscope, the longitudinal axis of the distal end section of the shaft being a longitudinal axis of the shaft. For example, the oblique-view endoscope objective may have a viewing direction of about 45°. If the negative lens has a recess that is asymmetric with respect to the optical axis of the negative lens, the negative lens may be mounted on the entrance face of the deflection prism such that a lateral direction of displacement of the recess with respect to the optical axis is in a half-plane formed by a longitudinal axis of the endoscope objective and the viewing direction.

According to a preferred embodiment of the endoscope objective, a viewing direction being defined by the optical axis of the negative lens forms an angle to the longitudinal axis of the endoscope objective. The entrance face of the deflection prism is substantially perpendicular to the optical axis of the negative lens, and the first reflective plane is inclined at about half the angle to the longitudinal axis of the endoscope objective. In particular, the deflection prism has only two reflective planes, which are the first reflective plane and the entrance face. Thus, the rays entering into the deflection prism through the entrance face are internally reflected twice and exit the deflection prism through the exit face. In this way an oblique-view endoscope objective having a simple and efficient optical design can be provided.

Most preferably, the endoscope objective is configured such that substantially all rays that enter into the deflection prism through the entrance face are directed by the reflection on the first reflective plane towards that part of the entrance face that is covered by a cavity formed between the negative lens and the entrance face, i.e. by the concave optical surface of the second face of the negative lens and, if present, by the recess. In that part of the entrance face the air layer enhances total reflection, thus improving the light collecting and imaging properties of the endoscope objective.

The features of the invention as mentioned above and as described below apply not only in the combinations mentioned but also in other combinations or alone, without leaving the scope of the present invention.

BRIEF DESCRIPTION OF THE DRAWINGS

Further aspects of the present invention will be apparent from the figures and from the description of a particular embodiment that follows.

DETAILED DESCRIPTION

Figure 1A:
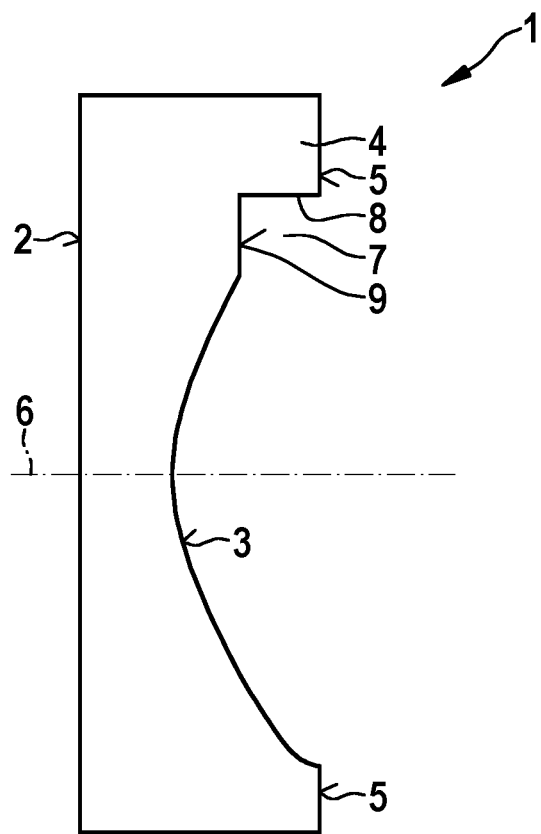
FIGS. 1a and 1b show a negative lens according to a first embodiment of the invention in an axial cross-section and in an axial view, respectively.

In FIG. 1a, a negative lens according to a first embodiment of the invention is depicted in an axial cross-section. The negative lens 1 has a first face with a planar optical surface 2 and a second face with a concave optical surface 3. The second face comprises an outer rim 4 having a ring-shaped planar surface 5 that is perpendicular to the optical axis 6 of the negative lens 1. Adjacent to the concave optical surface 3 and joining it, a recess 7 is formed having a step 8 and a planar back-surface 9. As can be seen in the axial view shown in FIG. 1b, the recess 7 extends to one side of the concave optical surface 3 only. The concave optical surface 3 and the recess 7 are encompassed by the planar surface 5.

Figure 1B:
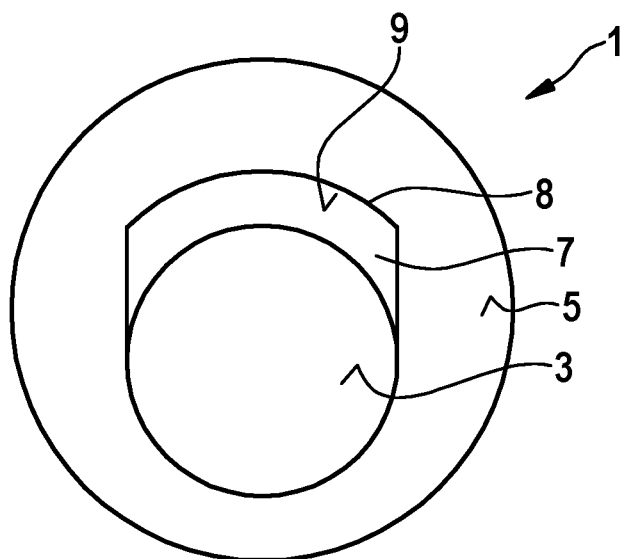
Figure 2A:
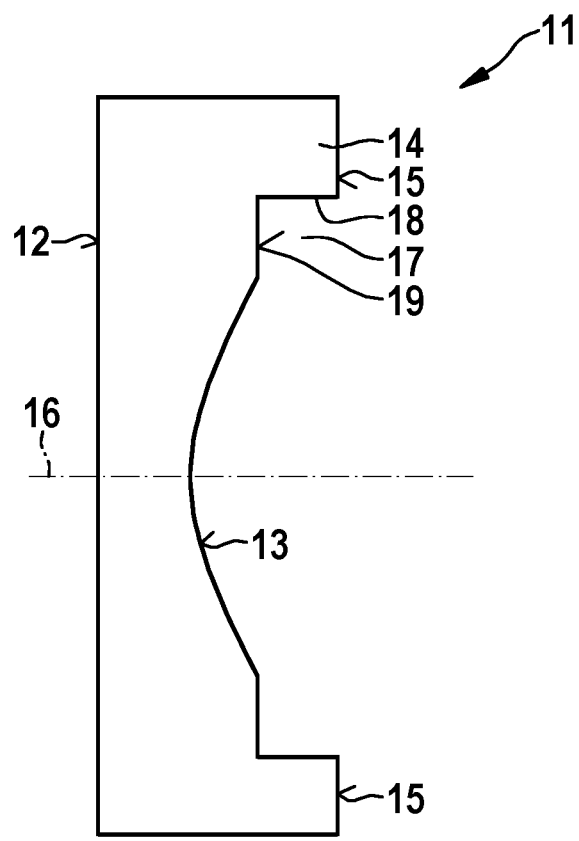
FIGS. 2a and 2b show a negative lens according to a second embodiment of the invention in an axial cross-section and in an axial view, respectively.
Figure 2B:
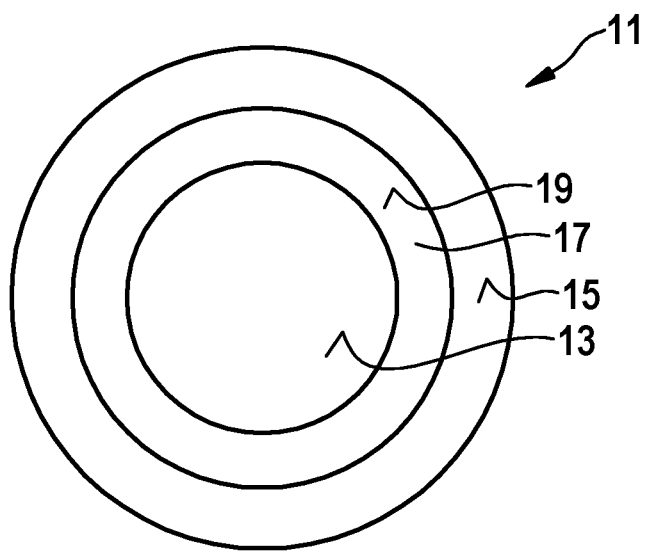

An alternative embodiment of the negative lens is shown in FIGS. 2a and 2b which depict the negative lens 11 in a similar way as described with respect to FIGS. 1a and 1b. The negative lens 11 is a plano-convex lens, having a planar surface 12 on a first face and a concave optical surface 13 on a second face. The negative lens 11 comprises a circumferential rim 14 having a ring-shaped planar surface 15 that is arranged symmetrically with respect to an optical axis 16 of the negative lens 11. In a symmetrical manner, a recess 17 is arranged on the inner side of the rim 14, being formed by a step 18 and a planar back-surface 19. The symmetrical structure of the negative lens 11 is seen clearly in FIG. 2b.

Figure 3:
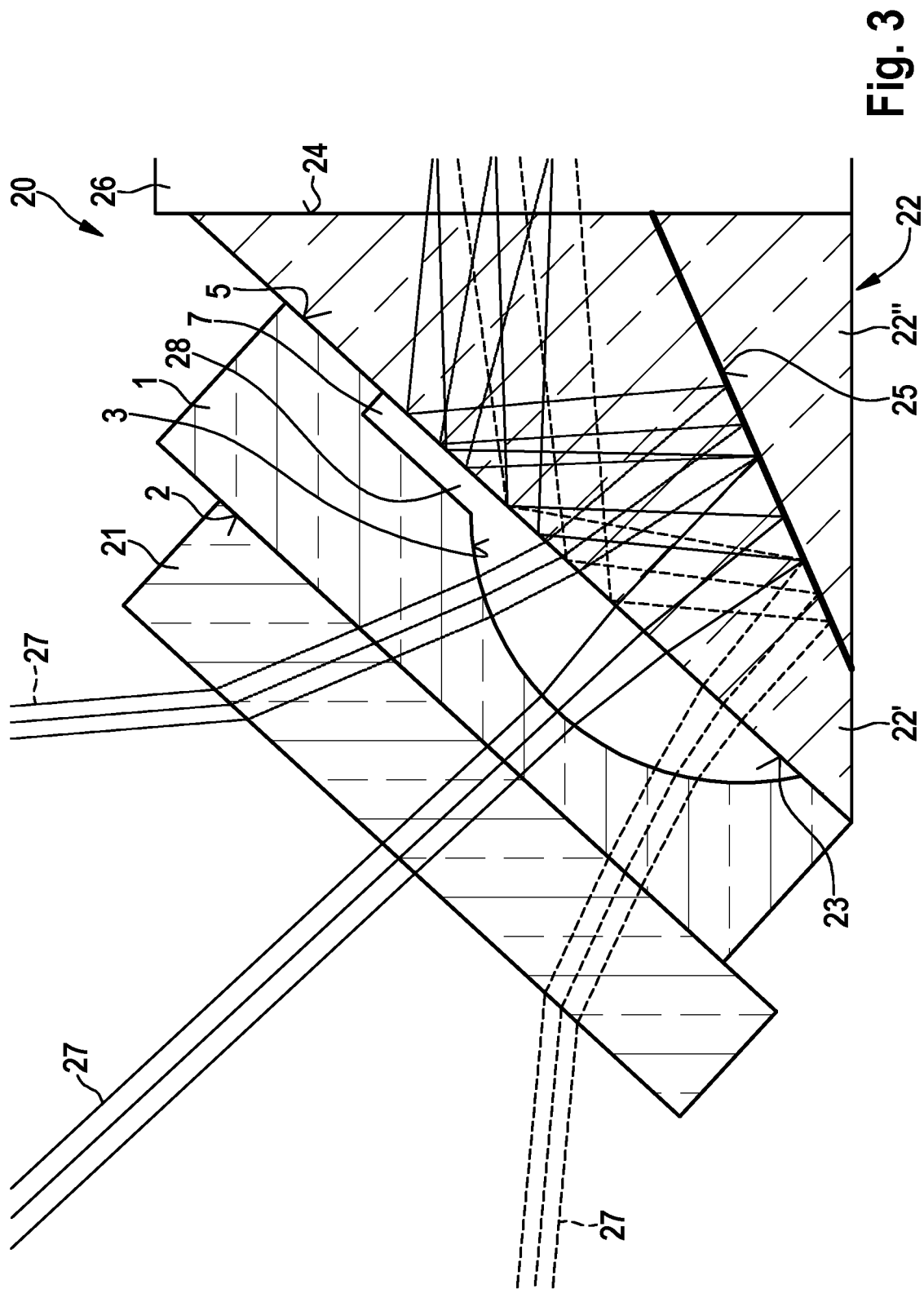
FIG. 3 shows a section of an endoscope objective comprising a negative lens according to the embodiment of FIGS. 1a and 1b in a longitudinal cross section.

In FIG. 3, a section of an oblique-view endoscope objective 20 is shown in a longitudinal cross section, illustrating in an exemplary manner how the negative lens 1 according to the embodiment of FIGS. 1a and 1b may be integrated into an endoscope objective 20. It is to be understood that instead, the negative lens 11 shown in FIGS. 2a and 2b could be employed in the endoscope objective 20. In FIG. 3 only a section of the oblique-view endoscope objective 20 is shown, the objective comprising further optical elements not shown.

The optical system of the endoscope objective 20 comprises a glass plate 21 forming a cover plate of the endoscope objective 20, a plano-concave negative lens 1 and a wedge-shaped deflection prism 22. The deflection prism 22 has an entrance face formed by a planar surface 23 and an exit face 24. The deflection prism 22 consists of two cemented prismatic elements 22', 22" having a planar interface 25. A first reflective plane of the deflection prism 22 is formed by the interface 25 which may comprise a reflective layer. A second reflective plane of the deflection prism 22 is formed by the planar surface 23, i.e. by the entrance face. The interface 25 is inclined with respect to a longitudinal direction of the endoscope objective by about half the angle at which the planar surface 23 is inclined. If the viewing direction is 45°, the planar surface is inclined at about α=45° to the longitudinal axis, and the interface at about α/2=22.5°. On its proximal side, the exit face 24 of the deflection prism 22 is cemented to a further optical element which may be a glass block 26 or a positive lens, for example. The negative lens 1 is cemented with its planar surface 4 upon the entrance face of the deflection prism 22, i.e. on the planar surface 23. The cover glass 21 is cemented on the planar optical surface 2 of the negative lens 1, but may be as well arranged with an air gap between the cover glass 21 and the negative lens 1. As shown in FIG. 3, the recess 7 is arranged on the planar surface 23 of the deflection prism 22 displaced from the concave optical surface 3 in a half-plane defined by the viewing direction and the longitudinal axis of the endoscope objective.

The incident rays 27 coming from an object field are transmitted through the glass plate 21, the negative lens 1 and the planar surface 23 to enter into the deflection prism 22, are reflected on the interface 25 of the deflection prism 22 towards the planar surface 23, and are totally reflected on the planar surface 23 of the deflection prism 22 into the direction of a longitudinal axis of the endoscope objective 20. Due to the cavity 28 formed by the concave optical surface 3 and the recess 7 extending to one side of the concave optical surface 3, that fraction of the area of the planar surface 23 that can be employed for total internal reflection is extended into a direction needed for a larger fraction of rays to be reflected into the proximal longitudinal direction.

Figure 4:
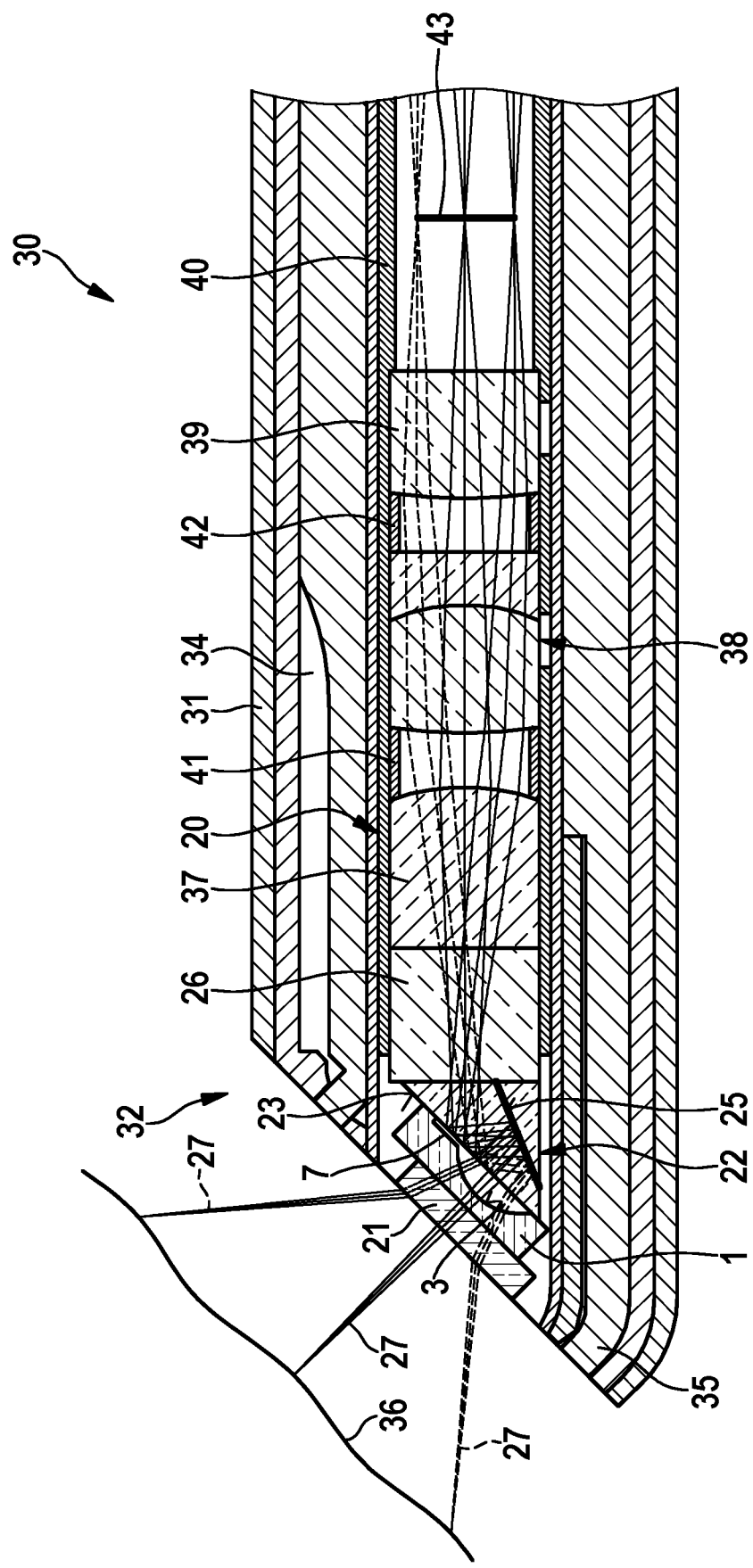
FIG. 4 shows a distal end section of an oblique-view endoscope comprising the objective of FIG. 3 in a longitudinal cross section.

In FIG. 4, the above described endoscope objective 20 as mounted in a distal end section of a shaft 30 of an oblique-view endoscope is shown in a longitudinal cross-section. The endoscope shaft 30 comprises a rigid outer shaft 31 having a distal end face 32 that is oblique to a longitudinal axis of the shaft 30, corresponding to an oblique viewing direction of, for example, 45°. The shaft 30 comprises an inner shaft 33 forming a space 34 between the inner shaft 33 and the outer shaft 31, the space 34 accommodating optical fibres 35 (not shown in detail) for transmitting illumination light to the distal end face 32 for illuminating an object field 36. The optical system of the endoscope objective 20 comprises the negative lens 1, the deflection prism 22, the glass block 26 (see FIG. 3) and further lenses 37, 38, 39 which may be single lenses or cemented doublets, for example. The lenses 39, 38, and a unit formed by the lens 37, glass block 26, deflection prism 22, and negative lens 1 are held in a distal end section of an optics tube 40; the last-mentioned unit may also comprise the glass plate 21. Appropriate air gaps between the lenses 37, 38, and 39 are maintained by ring-shaped spacers 41, 42. Further in a proximal direction the optics tube 40 may accommodate an arrangement of relay lenses (not shown).

Light rays 27 coming from the object field 36 enter into the endoscope objective 20 through glass plate 21 and are collected by negative lens 1. As described above (see FIG. 3), the light rays 27 enter through the planar surface 23 into the deflection prism 22, are back-reflected on the interface 25 and are reflected by total internal reflection on the planar surface 23 into a substantially axial direction. The rays are then transmitted through glass block 26 and are focused by positive lenses 37, 38, 39 into an image plane 43. The image formed in the image plane 43 is transmitted by relay lenses (not shown) to the proximal end of the endoscope. The negative lens 1 is cemented directly upon the planar surface 23 of the deflection prism 22. The deflection prism 22 that consists of two prismatic elements 22', 22" is cemented to the glass block 26. As depicted in FIG. 4, the recess 7 of the negative lens 1 is arranged such that the rays 27 are totally reflected on that part of the planar surface 23 of the deflection prism 22 on the distal side of which an air-filled space or air layer is formed by the concave optical surface 3 and the recess 7.

Figure 5:
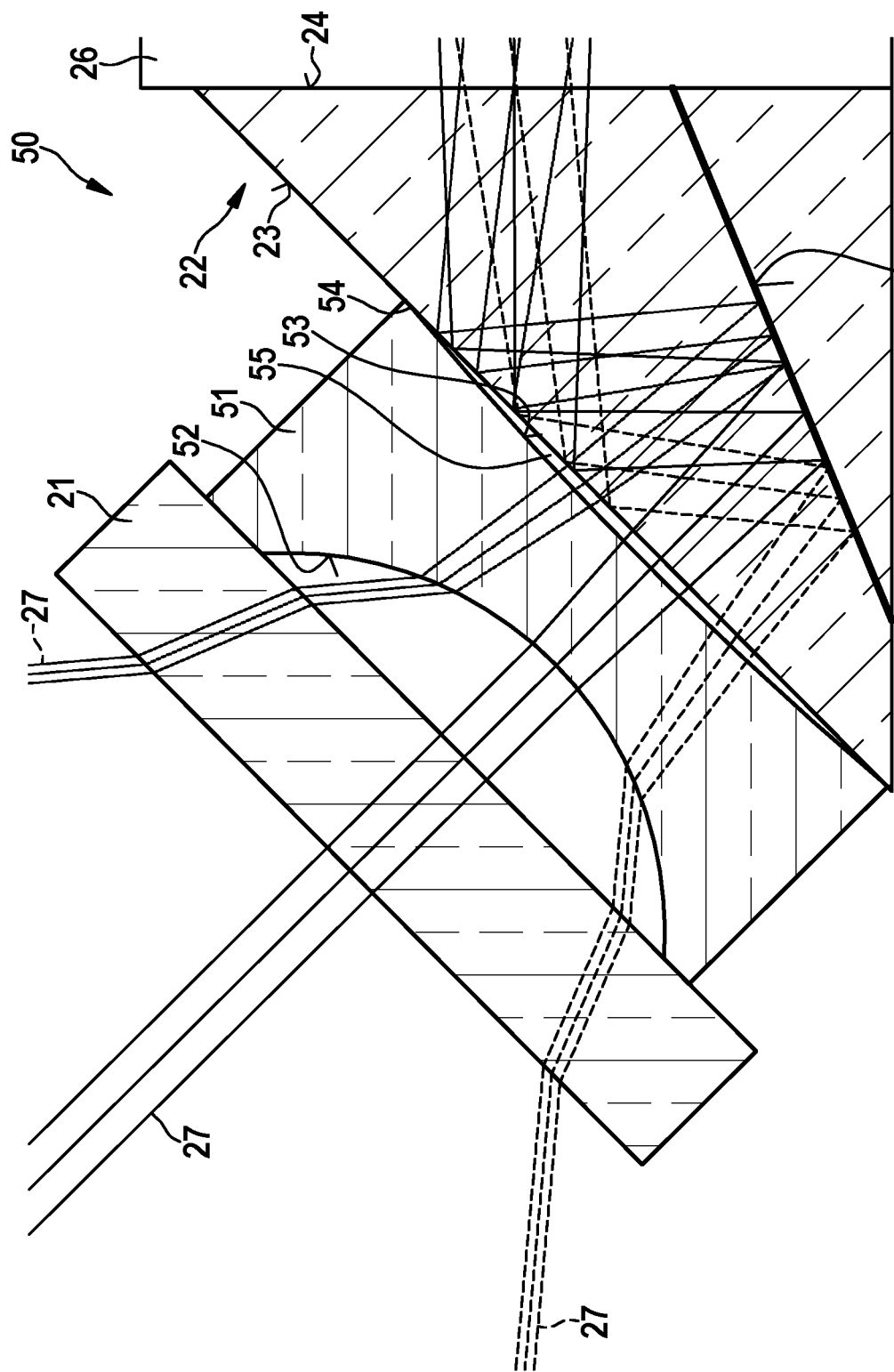
FIG. 5 shows a section of an endoscope objective according to a further embodiment of the invention in a longitudinal cross section.

In FIG. 5 a section of an endoscope objective 50 according to a further embodiment of the invention is shown in a view corresponding to that of FIG. 3. As opposed to the embodiment depicted in FIG. 3, in this case the negative lens 51 is a bi-concave lens, having a first concave optical surface 52 on its first face and a second concave optical surface 53 on its second face. The second concave optical surface 53 is encompassed by a closed rim 54 which may have a planar surface. As shown in FIG. 5, the negative lens 51 is directly cemented upon the first planar surface 23 of the deflection prism 22, the rim 54 abutting the planar surface 23 of the deflection prism 22. The other optical elements of the endoscope objective, including a glass plate 21 cemented upon an outer rim encompassing the first concave optical surface, are configured as described above (see FIGS. 3 and 4). As in that embodiment, the rays 27 are totally reflected on that part of the planar surface 23 of the deflection prism 22 which is covered by an air-filled space, however, in this case the air-filled space is provided by the cavity 55 formed by the second concave surface 53 only.

For clarity not all reference numerals are displayed in all figures. If a reference numeral is not explicitly mentioned in the description of a figure, it has the same meaning as in the other figures.

What is claimed is:

1. A negative lens, comprising:
    a first face;
    a second face opposite the first face;
    a cavity in the second face having a concave optical surface;
    a recess in the second face, the recess adjacent to the concave optical surface and enlarging the cavity;
    a rim encompassing the concave optical surface and the recess, the rim having a planar surface.

2. An endoscope objective, comprising:
    a deflection prism having an entrance face;
    the negative lens of claim 1 coupled to the deflection prism such that the rim contacts the entrance face.

3. An endoscope, comprising:
    a shaft having proximal and distal ends;
    the endoscope objective of claim 2 at the distal end of the shaft.

4. The endoscope of claim 3, wherein:
    the negative lens is adapted to collect rays from an object field to be observed;
    the rays pass through the negative lens and enter the deflection prism through the entrance face;
    the rays are reflected internally in the deflection prism towards the entrance face;
    the recess extends an area where the rays are reflected internally in the deflection prism.

5. The endoscope of claim 4, wherein substantially all rays entering the entrance face of the deflection prism are internally reflected on the entrance face at an area covered by the cavity.

6. The endoscope of claim 3, wherein the cavity is filled with air.

7. The endoscope of claim 3, wherein the distal end has a distal end face that is oblique to a longitudinal axis of the shaft and corresponds to an oblique viewing direction of the endoscope.

8. A method of manufacturing the negative lens of claim 1, comprising grinding the negative lens out of a block of transparent material.

9. An endoscope objective, comprising:
    a deflection prism having an entrance face;
    the negative lens of claim 1 coupled to the deflection prism such that the rim contacts the entrance face;
    wherein a back-surface of the recess extends radially from the cavity and is substantially parallel to the first face.

10. The endoscope objective of claim 9, wherein the negative lens comprises a plano-concave lens.

11. The endoscope objective of claim 9, wherein the recess is asymmetric with respect to the concave optical surface.

12. The endoscope objective of claim 11, wherein the recess extends from the concave optical surface in only one lateral direction.

13. The endoscope objective of claim 9, wherein the recess is symmetric with respect to the concave optical surface.

14. The endoscope objective of claim 13, wherein the recess comprises a step-shaped depression.

15. The endoscope objective of claim 9, wherein the negative lens is formed in one piece.

16. The endoscope objective of claim 9, wherein:
    an optical axis of the negative lens forms an angle $\alpha$ to a longitudinal axis of the endoscope objective;
    the entrance face of the deflection prism is substantially perpendicular to the optical axis of the negative lens;
    a first reflective plane of the deflection prism is inclined at about $\alpha/2$ to the longitudinal axis of the endoscope objective.

17. An endoscope objective, comprising:
    a negative lens having a first face with a first rim encompassing a first concave optical surface, a second face opposite the first face with a second rim encompassing a second concave optical surface;
    a deflection prism having an entrance face, the deflection prism coupled to the negative lens such that the second rim contacts the entrance face;
    a glass plate coupled to and in contact with the first rim of the negative lens.

18. An endoscope, comprising:
    a shaft having proximal and distal ends;
    the endoscope objective of claim 17 at the distal end of the shaft.

19. An endoscope, comprising:
a shaft having proximal and distal ends;
an endoscope objective at the distal end of the shaft, the endoscope objective having:
- a negative lens having:
  - a first face;
  - a second face opposite the first face;
  - a cavity in the second face having a concave optical surface;
  - a recess in the second face, the recess adjacent to the concave optical surface and enlarging the cavity;
  - a rim encompassing the concave optical surface and the recess, the rim having a planar surface;
- a deflection prism having an entrance face;
- the negative lens coupled to the deflection prism such that the rim contacts the entrance face;
- a distal end face at the distal of the shaft is oblique to a longitudinal axis of the shaft and corresponds to an oblique viewing direction of the endoscope;
- wherein the negative lens is adapted to collect rays from an object field to be observed;
- the rays pass through the negative lens and enter the deflection prism through the entrance face;

the rays are reflected internally in the deflection prism towards the entrance face;
- the recess extends an area where the rays are reflected internally in the deflection prism.

20. The endoscope of claim 19, wherein substantially all rays entering the entrance face of the deflection prism are internally reflected on the entrance face at an area covered by the cavity.

* * * * *